United States Patent [19]

Takematsu et al.

[11] Patent Number: 5,468,719
[45] Date of Patent: Nov. 21, 1995

[54] N-ACYL-N-PHENYLTETRAHYDRO-PHTHALAMIC ACID DERIVATIVES, METHODS OF PRODUCING SAME, AND HERBICIDES CONTAINING SAME AS EFFECTIVE COMPONENTS

[75] Inventors: Tetsu Takematsu, Utsunomiya; Takeo Komata; Takashi Kume, both of Kawagoe; Kiyoshi Suzuki, Utsunomiya; Matsue Kawamura, Kawagoe; Yumiko Shirakawa, Kawagoe; Kaoru Mori, Kawagoe, all of Japan

[73] Assignee: Central Glass Company, Limited, Yamaguchi, Japan

[21] Appl. No.: 133,200

[22] PCT Filed: Feb. 26, 1993

[86] PCT No.: PCT/JP93/00245

§ 371 Date: Oct. 22, 1993

§ 102(e) Date: Oct. 22, 1993

[87] PCT Pub. No.: WO93/17005

PCT Pub. Date: Feb. 9, 1993

[30] Foreign Application Priority Data

Feb. 26, 1992 [JP] Japan .................................. 4-039809

[51] Int. Cl.[6] ........................ A01N 43/04; C07D 265/36
[52] U.S. Cl. ................................................ 504/224; 544/105
[58] Field of Search ............................ 504/224; 544/105

[56] References Cited

FOREIGN PATENT DOCUMENTS

0415641A1 8/1990 European Pat. Off. .
0454444A1 4/1991 European Pat. Off. .
4-501567 3/1992 Japan .
WO90/15057 12/1990 WIPO .

*Primary Examiner*—John M. Ford
*Attorney, Agent, or Firm*—Keck, Mahin & Cate

[57] ABSTRACT

The invention provides N-acyl-N-phenyltetrahydrophthalamic acid derivatives represented by the general formula [I], methods of producing the same, herbicides containing the same as the effective components, imidoylchloride derivatives as the intermediate products and methods of producing the same,

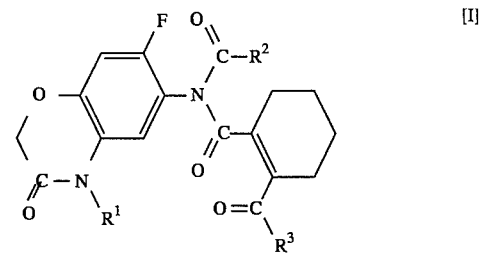

wherein $R^1$ represents an alkyl group, an alkenyl group, an alkynyl group, an alkoxyalkyl group, a haloalkyl group, a haloalkenyl group, a haloalkynyl group or a cyanoalkyl group, $R^2$ represents a lower alkyl group or a halogenated lower alkyl group, and $R^3$ represents a lower alkoxy group, a lower alkenyloxy group, a lower alkynyloxy group, a lower alkoxyalkoxy group, a substituted or unsubstituted benzyloxy group, a lower haloalkyloxy group or a lower alkoxycarbonylalkoxy group. The herbicides of the present invention, which are very useful, can be widely applied to upland, paddy field, orchard, turf, forest, non-crop land, etc., and are not harmful to crops.

36 Claims, No Drawings

N-ACYL-N-PHENYLTETRAHYDRO-PHTHALAMIC ACID DERIVATIVES, METHODS OF PRODUCING SAME, AND HERBICIDES CONTAINING SAME AS EFFECTIVE COMPONENTS

TECHNOLOGICAL FIELD

This invention relates to N-acyl-N-phenyltetrahydrophthalamic acid derivatives which are novel compounds, to methods of producing the same and to herbicides containing the same as the effective components, and to imidoylchloride derivatives as intermediate products and to methods of producing the same. N-acyl-N-phenyltetrahydrophthalamic acid derivatives of the present invention exhibit excellent herbicidal activity. The derivatives are useful as a herbicide which can be widely applied to upland, paddy field, orchard, pasture, turf, forest, non-crop land, etc. The derivatives are not harmful to crops.

BACKGROUND TECHNOLOGY

Hitherto, herbicidal activity of tetrahydrophthalamic acid derivatives has been well known. For example, N-(4'-chlorophenyl)- 3, 4, 5, 6-tetrahydrophthalamic acid methyl ester is known, as is disclosed in JP-A (Patent) 48-44425.

However, the conventional tetrahydrophthalamic acid derivatives are not necessarily sufficient in herbicidal activity, or are substantially limited in herbicidal spectrum against weeds. Furthermore, these derivatives are insufficient in selectivity between crops and weeds, thereby inducing problems of safety for crops.

It is an object of the present invention to solve the aforementioned problems, and to provide novel compounds which are excellent in herbicidal activity but not harmful to crops, methods of producing the same and herbicides containing the same as the effective components, and intermediate products and methods of producing the same.

DISCLOSURE OF THE INVENTION

The inventors have found and already proposed that novel tetrahydrophthalamic acid derivatives each having a specific substituent acyl group bonded to an amide nitrogen atom are very excellent in herbicidal activity, selectivity and herbicidal spectrum (International Application PCT/JP91/01109). In view of this, the inventors have intensely studied, and as a result have completed the present invention.

The present invention provides N-acyl-N-phenyltetrahydrophthalamic acid derivatives represented by the general formula [I], methods of producing the same, and herbicides containing the same as the effective components:

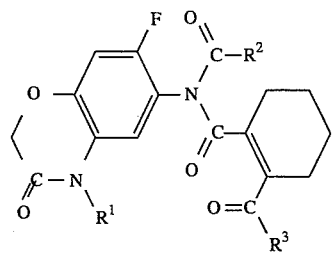

wherein $R^1$ represents an alkyl group, an alkenyl group, an alkynyl group, an alkoxyalkyl group, a haloalkyl group, a haloalkenyl group, a haloalkynyl group or a cyanoalkyl group, $R^2$ represents a lower alkyl group or a halogenated lower alkyl group, and $R^3$ represents a lower alkoxy group, a lower alkenyloxy group, a lower alkynyloxy group, a lower alkoxyalkoxy group, a substituted or unsubstituted benzyloxy group, a lower haloalkyloxy group or a lower alkoxycarbonylalkoxy group.

Furthermore, the present invention provides imidoylchloride derivatives represented by the general formula [II] and methods of producing the same:

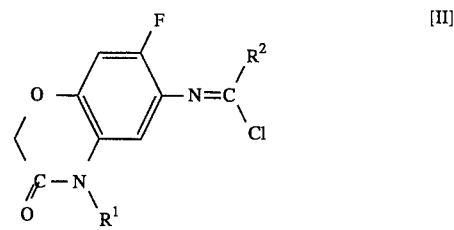

wherein $R^1$ represents an alkyl group, an alkenyl group, an alkynyl group, an alkoxyalkyl group, a haloalkyl group, a haloalkenyl group, a haloalkynyl group or a cyanoalkyl group, $R^2$ represents a lower alkyl group or a halogenated lower alkyl group.

N-acyl-N-phenyltetrahydrophthalamic acid derivatives [I] of the present invention can be produced, for example, as is shown by the following formula, by reacting imidoylchloride derivatives represented by the general formula [II] with carboxylic acids represented by the general formula [III].

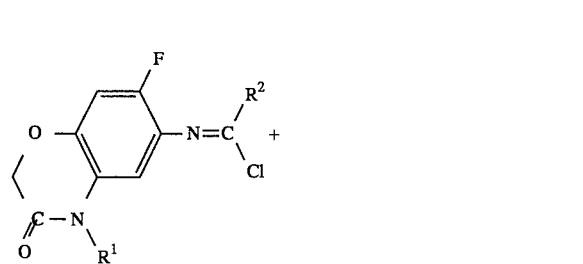

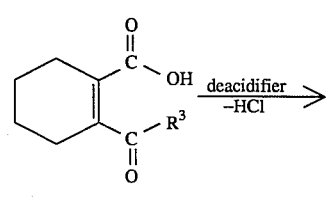

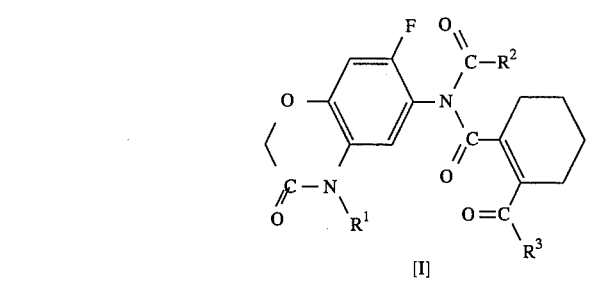

wherein $R^1$ represents an alkyl group, an alkenyl group, an alkynyl group, an alkoxyalkyl group, a haloalkyl group, a haloalkenyl group, a haloalkynyl group or a cyanoalkyl group, $R^2$ represents a lower alkyl group or a halogenated lower alkyl group, and $R^3$ represents a lower alkoxy group, a lower alkenyloxy group, a lower alkynyloxy group, a lower alkoxyalkoxy group, a substituted or unsubstituted benzyloxy group, a lower haloalkyloxy group or a lower alkoxycarbonylalkoxy group.

The reaction can proceeds preferably in a suitable solvent such as benzene, toluene, xylene, methylene chloride, chloroform, ethyl acetate, dioxane, tetrahydrofuran, diethyl ether, dimethylformamide or dimethylsulfoxide, by adding a suitable deacidifying agent such as an organic base such as triethylamine or pyridine, or an inorganic base such as potassium hydroxide or sodium hydroxide.

The reaction temperature is not particularly limited, but is usually from 0° C. to 200° C., and a preferred range is from 40° C. to 100° C.

Furthermore, N-acyl-N-phenyltetrahydrophthalamic acid derivatives [I] of the present invention can be produced, as is shown by the following formula, by reacting imidoylchloride derivatives represented by the general formula [II] with alkali metal salts of carboxylic acids represented by the general formula [V], too.

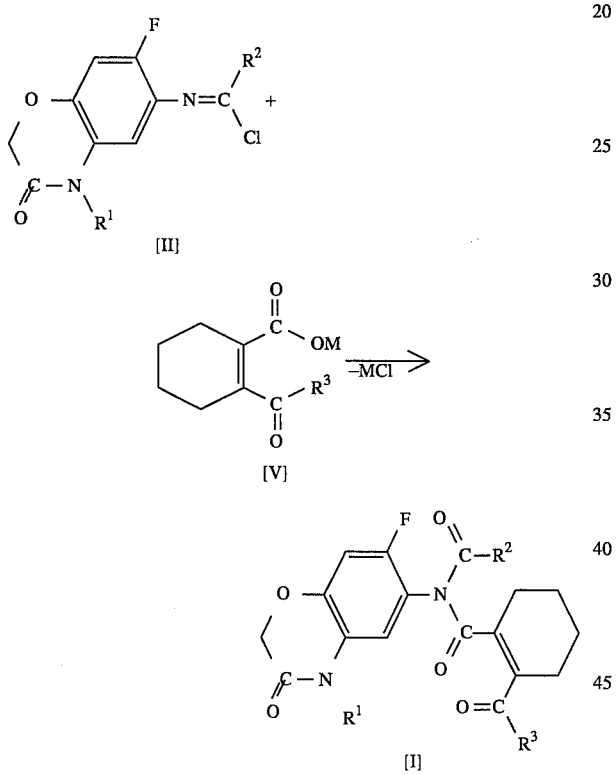

wherein $R^1$ represents an alkyl group, an alkenyl group, an alkynyl group, an alkoxyalkyl group, a haloalkyl group, a haloalkenyl group, a haloalkynyl group or a cyanoalkyl group, $R^2$ represents a lower alkyl group or a halogenated lower alkyl group, $R^3$ represents a lower alkoxy group, a lower alkenyloxy group, a lower alkynyloxy group, a lower alkoxyalkoxy group, a substituted or unsubstituted benzyloxy group, a lower haloalkyloxy group or a lower alkoxycarbonylalkoxy group, and M represents an alkali metal.

The reaction can proceeds in a suitable solvent such as benzene, toluene, xylene, methylene chloride, chloroform, ethyl acetate, dioxane, tetrahydrofuran, diethyl ether, dimethylformamide and dimethylsulfoxide or water, by adding, if necessary, a phase transfer catalyst such as a quaternary ammonium salt.

The reaction temperature is not particularly limited, but is usually from 0° C. to 200° C., and a preferred range is from 0° C. to 100° C.

Furthermore, imidoylchloride derivatives [II] which are necessary as a starting material to obtain N-acyl-N-phenyltetrahydrophthalamic acid derivatives [I] of the present invention can be produced, according to the following reaction formula, by the reaction of anilide derivatives which are represented by the general formula [IV], using a dehydrochlorinating agent, in the presence of a reaction solvent or not.

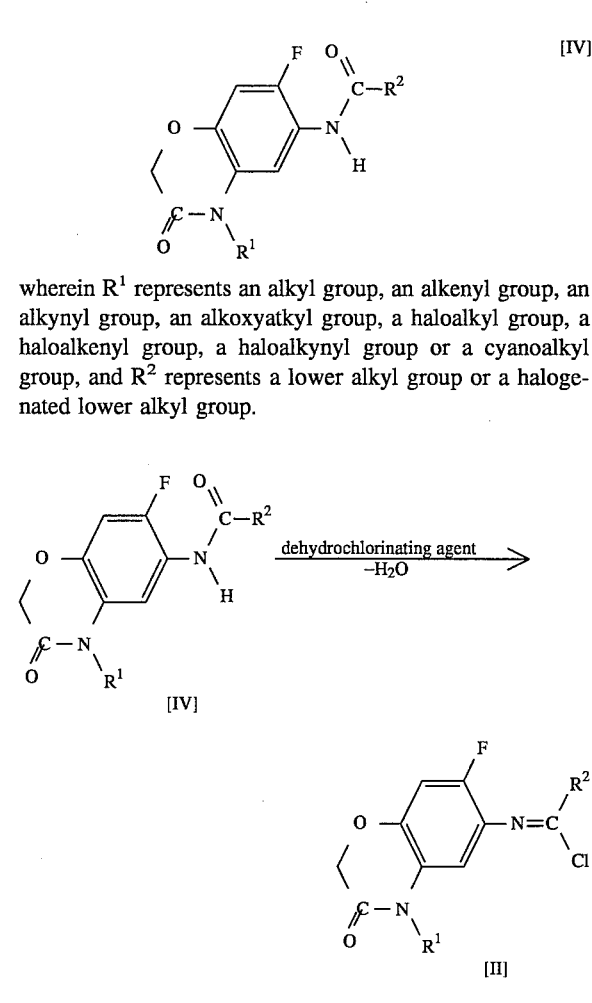

wherein $R^1$ represents an alkyl group, an alkenyl group, an alkynyl group, an alkoxyalkyl group, a haloalkyl group, a haloalkenyl group, a haloalkynyl group or a cyanoalkyl group, and $R^2$ represents a lower alkyl group or a halogenated lower alkyl group.

As preferable examples of the dehydrochlorinating agent used in the reaction, phosphorus pentachloride, phosphorus trichloride-chlorine, thionyl chloride, arylsulfonylchloride, phosgene, triphenylphosphine-carbon tetrachloride and polymer carried triphenylphosphine-carbon tetrachloride can be cited.

Furthermore, as preferable examples of the solvent used in the reaction, halogenated hydrocarbons such as dichloroethane, carbon tetrachloride, chloroform and methylene chloride, aromatic hydrocarbons such as benzene, toluene, xylene and chlorobenzene, polar solvents such as acetonitrile and dimethyl sulfoxide, etc. can be cited.

The reaction temperature is not particularly limited, but is preferably in the range from 0° to 100° C.

THE BEST MODE TO CARRY OUT THE INVENTION

Hereinafter, the present invention will be described concretely with reference to Examples.

EXAMPLE 1

Synthesis of
N-(7fluoro-4-propargyl-2H-1,4-benzoxazine-
3(4H)-one-6-yl)-2-chloroacetimidoylchloride (A
compound which is represented by No. 2 in Table
1 and by the general formula [II])

First, 1.00 g of N-(7-fluoro-4-propargyl-2H-1,4-benzoxazine- 3(4H)-one-6-yl)-2-chloroacetamide, 2.25 g of triphenylphosphine polymer bound and 4 ml of carbon tetrachloride were dissolved in 35 ml of 1,2-dichloroethane, and then the reflux under heat was continued for 2 hr. After letting the solution stand to cool the same, the solid was filtered out, and then the solvent was distilled out under reduced pressure to quantitatively obtain N-(7-fluoro-4-propargyl-2H-1,4-benzoxazine-3(4H)-one- 6-yl)-2-chloroacetimidoylchloride.

EXAMPLE 2

Synthesis of
N-(2-chloroacetyl)-N-(7-fluoro-4propargyl-
2H-1,4-benzoxazine-3(4H)-one-6-yl)-
3,4,5,6-tetrahydrophthalamic acid methyl ester (A
compound which is represented by No. 5 in Table
3 and by the general formula [I])

First, 1.06 g of N-(7-fluoro-4-propargyl-2H- 1,4-benzoxazine-3(4H)-one-6-yl)-2-chloroacetimidylchloride and 0.62 g of 3,4,5,6-tetrahydrophthalamic acid monomethyl ester were dissolved in 50 ml of benzene, and 0.38 g of triethylamine was added to the solution at room temperature. After that the stirring was continued for 2 hr at 60° C. After letting the reaction liquid stand to cool the same, it was poured into cool water, and then the organic layer was separated therefrom. The organic layer was washed first with water and then with saturated brine, and then dried by using anhydrous magnesium sulfate. The solvent was concentrated, and then methanol was added to the residue. The produced crystals were filtered out, then washed with methanol, and then dried to obtain 1.0 g of N-(2-chloroacetyl)-N-(7-fluoro-4-propargyl-2H- 1,4-benzoxazine-3(4H)-one-6-yl)-3,4,5,6-tetrahydrophthalamic acid methyl ester. The melting point was 156°–158° C.

EXAMPLE 3

Synthesis of N-(7-fluoro-4-propargyl-2H-
1,4-benzoxazine-3(4H)-one-6-yl)-acetimidoylchloride
(A compound which is represented by No. 3 in
Table 1 and by the general formula [II])

First, 10 ml of benzene and 0.4 g of phosphorus pentachloride were added to 0.5 g of N-(7-fluoro- 4-propargyl-2H-1,4-benzoxazine-3(4H)-one-6-yl)-acetamide, and the stirring was continued for 1.0 hr at 60° C. After letting the mixture stand to cool the same, the produced phosphorus oxychloride and benzene were distilled out under reduced pressure to quantitatively obtain N-( 7-fluoro-4-propargyl-2H-1,4-benzoxazine-3(4H)-one-6-yl)-acetimidoylchloride.

EXAMPLE 4

Synthesis of N-acetyl-N-(7-fluoro-4-propargyl-
2H-1,4-benzoxazine-3(4H)-one-6=yl)-
3,4,5,6-tetrahydrophthatamic acid methyl ester (A
Compound which is represented by No. 14 in Table
3 and by the general formula [I])

First, 0.44 g of N-(7-fluoro-4-propargyl-2H- 1,4-benzoxazine-3(4H)-one-6-yl)-acetimidoylchloride and 0.29 g of 3,4,5,6-tetrahydrophthalamic acid monomethyl ester were dissolved in 15 ml of benzene, and 0.17 g of triethylamine was added to the solution at room temperature. After that the stirring was continued for 2 hr at 60° C. After letting the reaction liquid stand to cool the same, it was poured into cool water, and then the organic layer was separated therefrom. The organic layer was washed first with water and then with saturated brine, and then dried by using anhydrous magnesium sulfate. The solvent was concentrated, and then the residue was treated by silica gel column chromatography (development solvent: ethyl acetate/n-hexane) to obtain N-acetyl-N-(7-fluoro- 4-propargyl-2H-1,4-benzoxazine-3(4H)-one-6-yl)- 3,4,5,6tetrahydrophthalamic acid methyl ester. The melting point was 153°–154° C.

Table 3 shows N-acyl-N-phenyltetrahydrophthalamic acid derivatives [I] of the present invention, each of which was obtained by a process analogous to the processes of the foregoing examples, and Table 4 shows $^1$H-NMR absorption spectrum values thereof. Table 1 shows imidoylchloride derivatives [II], and Table 2 shows $^1$H-NMR absorption spectrum values thereof. However, the compounds of the present invention are not limited to those shown in Tables 1 to 4.

The compound Nos. in Tables 1 to 4 will be employed in the following examples and experiments.

TABLE 1

| Compound No. | $R^1$ | $R^2$ |
| --- | --- | --- |
| 1 | $CH_2CN$ | $CH_2Cl$ |
| 2 | $CH_2C{\equiv}CH$ | $CH_2Cl$ |
| 3 | $CH_2C{\equiv}CH$ | $CH_3$ |
| 15 | $CH_2CH_3$ | $CH_3$ |
| 16 | $CH(CH_3)_2$ | $CH_3$ |
| 17 | $CH_2CH_2F$ | $CH_3$ |
| 18 | $CH_2CH_2OCH_3$ | $CH_3$ |
| 19 | $CH_2CH{=}CH_2$ | $CH_3$ |
| 20 | $CH(CH_3)C{\equiv}CH$ | $CH_3$ |

TABLE 2

| Compound No. | $^1$H-NMR Absorption Spectrum Values (δ) (in $CDCl_3$) |
| --- | --- |
| 1 | 4.53(s, 2H), 4.7(s, 2H), 4.75(m, 2H), 6.89(d, J=10Hz, 1H), 6.91(d, J=7Hz, 1H) |
| 2 | 2.3(t, J=2Hz, 1H), 4.5(s, 2H), 4.65(s, 2H), 4.7(m, 2H), 6.84(d, J=10Hz, 1H), 6.86(d, J=7Hz, 1H) |
| 3 | 2.3(t, J=2Hz, 1H), 2.63(s, 3H), 4.65(s, 4H), 6.71(d, J=7Hz, 1H), 6.80(d, J=10Hz, 1H) |
| 15 | 1.29(t, J=7Hz, 3H), 2.65(s, 3H), 3.9(q, J=7Hz, 2H), 4.62(s, 2H), 6.73(d, J=7Hz, 1H), 6.96(d, J=10Hz, 1H) |
| 16 | 1.5(d, J=7Hz, 6H), 2.6(s, 3H), 4.48(s, 2H), 4.5–5.0(m, 1H), 6.69(d, J=7Hz, 1H), 6.79(d, J=10Hz, 1H) |
| 17 | 2.6(s, 3H), 3.9–4.1(m, 1H), 4.15–4.25(m, 2H), 4.61(s, 2H), 4.8–5.0(m, 1H), 6.71(d, J=7Hz, 1H), 6.8(d, J=10Hz, 1H) |
| 18 | 2.62(s, 3H), 3.35(s, 3H), 3.5–3.7(m, 2H), 3.9–4.1(m, 2H), 4.61(s, 2H), 6.7(d, J=7Hz, 1H), 6.73(d, J=10Hz, 1H) |
| 19 | 2.56(s, 3H), 4.4–4.6(m, 2H), 4.57(s, 2H), 5.0–5.4(m, |

TABLE 2-continued

| Compound No. | $^1$H-NMR Absorption Spectrum Values (δ) (in CDCl$_3$) |
|---|---|
|  | 2H), 5.6~6.0(m, 1H), 6.5(d, J=7Hz, 1H), 6.75(d, J=10Hz, 1H) |
| 20 | 1.6(d, J=7Hz, 3H), 2.13(s, 1H), 2.16(s, 3H), 4.55(s, 2H), 4.85~5.2(m, 1H), 6.27(d, J=7Hz, 1H), 6.77(d, J=10Hz, 1H) |

TABLE 4

| Compound No. | $^1$H-NMR Absorption Spectrum Values (δ) (in CDCl$_3$) |
|---|---|
| 4 | 1.4~1.7(m, 4), 2.15~2.45(m, 4H), 3.8(s, 3H), 4.6(s, 2H), 4.78(s, 2H), 4.8(m, 2H), 6.95(d, J=10Hz, 1H), 7.38(d, J=7Hz, 1H) |
| 5 | 1.4~1.7(m, 4H), 2.15~2.45(m, 5H), 3.79(s, 3H), 4.57(s, 2H), 4.65(m, 2H), 4.73(s, 2H), 6.9(d, J=10Hz, 1H), 7.33(d, J=7Hz, 1H) |

TABLE 3

| Compound No. | R$^1$ | R$^2$ | R$^3$ | m.p. (°C.) |
|---|---|---|---|---|
| 4 | CH$_2$CN | CH$_2$Cl | OCH$_3$ | 181~183 |
| 5 | CH$_2$C≡CH | CH$_2$Cl | OCH$_3$ | 156~158 |
| 6 | CH$_2$C≡CH | CH$_2$Cl | OCH$_2$C≡CH | 142~143 |
| 7 | CH$_2$C≡CH | CH$_2$Cl | OCH$_2$(CH$_2$)$_2$CH$_3$ | 110~111 |
| 8 | CH$_2$C≡CH | CH$_2$Cl | OCH$_2$-C$_6$H$_5$ | 166.5~167.5 |
| 9 | CH$_2$C≡CH | CH$_2$Cl | OCH$_2$CH$_3$ | 154.5~155.5 |
| 10 | CH$_2$C≡CH | CH$_2$Cl | OCH$_2$CO$_2$CH$_2$CH$_3$ | 138~139 |
| 11 | CH$_2$C≡CH | CH$_2$Cl | OCH$_2$CH=CH$_2$ | 127.5~128.5 |
| 12 | CH$_2$C≡CH | CH$_2$Cl | OCH$_2$CH$_2$OCH$_3$ | 96~98 |
| 13 | CH$_2$C≡CH | CH$_2$Cl | OCH(CH$_3$)$_2$ | 84~86 |
| 14 | CH$_2$C≡CH | CH$_3$ | OCH$_3$ | 153~154 |
| 21 | CH$_2$C≡CH | CH$_3$ | OCH$_2$(CH$_2$)$_2$CH$_3$ | 90~91 |
| 22 | CH$_2$C≡CH | CH$_3$ | OCH$_2$-C$_6$H$_5$ | 155~156 |
| 23 | CH$_2$C≡CH | CH$_3$ | OCH$_2$CH$_2$OCH$_3$ | 90~91 |
| 24 | CH$_2$C≡CH | CH$_3$ | OCH(CH$_3$)$_2$ | oil-like substance |
| 25 | CH$_2$C≡CH | CH$_3$ | OCH(CH$_3$)CH$_2$OCH$_3$ | 115~116 |
| 26 | CH$_2$CH$_3$ | CH$_3$ | OCH$_3$ | oil-like substance |
| 27 | CH$_2$CH$_3$ | CH$_3$ | OCH(CH$_3$)$_2$ | 114~115 |
| 28 | CH(CH$_3$)$_2$ | CH$_3$ | OCH$_3$ | oil-like substance |
| 29 | CH(CH$_3$)$_2$ | CH$_3$ | OCH(CH$_3$)CH$_2$OCH$_3$ | oil-like substance |
| 30 | CH$_2$CH$_2$F | CH$_3$ | OCH$_3$ | 141~142 |
| 31 | CH$_2$CH$_2$F | CH$_3$ | OCH$_2$CH$_2$OCH$_3$ | oil-like substance |
| 32 | CH$_2$CH$_2$OCH$_3$ | CH$_3$ | OCH$_3$ | 92~93 |
| 33 | CH$_2$CH$_2$OCH$_3$ | CH$_3$ | OCH$_2$CH$_2$OCH$_3$ | oil-like substance |
| 34 | CH$_2$CH=CH$_2$ | CH$_3$ | OCH$_2$CH$_2$OCH$_3$ | oil-like substance |
| 35 | CH(CH$_3$)C≡CH | CH$_3$ | OCH$_2$CH$_2$OCH$_3$ | oil-like substance |

TABLE 4-continued

| Compound No. | ¹H-NMR Absorption Spectrum Values (δ) (in CDCl₃) |
|---|---|
| 6 | 1.4–1.7(m, 4H), 2.15–2.45(m, 5H), 2.52(t, J=2Hz, 1H), 4.56(s, 2H), 4.64(m, 2H), 4.7(m, 2H), 4.77(d, J=2Hz, 2H), 6.87(d, J=10Hz, 1H), 7.28(d, J=7Hz, 1H) |
| 7 | 0.92(t, J=7Hz, 3H), 1.2–1.7(m, 8H), 2.15–2.45(m, 5H), 4.14(t, J=7Hz, 2H), 4.53(s, 2H), 4.6(m, 2H), 4.68(s, 2H), 6.86(d, J=10Hz, 1H), 7.3(d, J=7Hz, 1H) |
| 8 | 1.4–1.7(m, 4H), 2.18(t, J=2Hz, 1H), 2.15–2.45(m, 4H), 4.42(bs, 2H), 4.56(m, 2H), 4.69(s, 2H), 5.2(s, 2H), 6.86(d, J=10Hz, 1H), 7.25(d, J=7Hz, 1H), 7.35(s, 5H) |
| 9 | 1.3(t, J=7Hz, 3H), 1.4–1.7(m, 4H), 2.15–2.45(m, 5H), 4.23(q, J=7Hz, 2H), 4.56(s, 2H), 4.67(m, 2H), 4.71(s, 2H), 6.88(d, J=10Hz, 1H), 7.32(d, J=7Hz, 1H) |
| 10 | 1.29(t, J=7Hz, 3H), 1.4–1.7(m, 4H), 2.25(t, J=2Hz, 1H), 2.15–2.45(m, 4H), 4.24(q, J=7Hz, 2H), 4.56(bs, 2H), 4.64(m, 2H), 4.7(s, 4H), 6.87(d, J=10Hz, 1H), 7.34(d, J=7Hz, 1H) |
| 11 | 1.4–1.7(m, 4H), 2.15–2.45(m, 5H), 4.57(s, 2H), 4.65(bs, 2H), 4.71(s, 4H), 5.16–5.48(m, 2H), 5.75–6.2(m, 1H), 6.89(d, J=10Hz, 1H), 7.29(d, J=7Hz, 1H) |
| 12 | 1.4–1.7(m, 4H), 2.15–2.45(m, 5H), 3.36(s, 3H), 3.64(t, J=6Hz, 2H), 4.33(t, J=6Hz, 2H), 4.64(m, 2H), 4.69(s, 2H), 4.71(s, 2H), 6.88(d, J=10Hz, 1H), 7.34(d, J=7Hz, 1H) |
| 13 | 1.28(d, J=6Hz, 6H), 1.4–1.7(m, 4H), 2.15–2.45(m, 5H), 4.54(s, 2H), 4.63(bs, 2H), 4.71(s, 2H), 5.08(m, 1H), 6.88(d, J=10Hz, 1H), 7.36(d, J=7Hz, 1H) |
| 14 | 1.4–1.7(m, 4H), 2.15–2.45(m, 5H), 2.2(s, 3H), 3.78(s, 3H), 4.73(m, 4H), 6.94(d, J=10Hz, 1H), 7.41(d, J=7Hz, 1H) |
| 21 | 0.92(t, J=6Hz, 3H), 1.5–1.8(m, 8H), 2.1–2.4(m, 5H), 2.25(s, 3H), 4.14(t, J=6Hz, 2H), 4.5–4.7(m, 2H), 4.68(s, 2H), 6.85(d, J=10Hz, 1H), 7.39(d, J=7Hz, 1H) |
| 22 | 1.6–1.8(m, 4H), 2.18(s, 3H), 2.3–2.5(m, 5H), 4.6–4.75(m, 2H), 4.68(s, 2H), 5.2(s, 2H), 6.85(d, J=10Hz, 1H), 7.33(s, 5H) |
| 23 | 1.45–1.7(m, 4H), 2.1–2.45(m, 5H), 2.31(s, 3H), 3.35(s, 3H), 3.6(m, 2H), 4.3(m, 2H), 4.5–4.7(m, 2H), 4.69(s, 2H), 6.85(d, J=10Hz, 1H), 7.42(d, J=7Hz, 1H) |
| 24 | 1.21(d, J=7Hz, 6H), 1.45–1.75(m, 4H), 2.05–2.45(m, 5H), 2.2(s, 3H), 4.45–4.8(m, 2H), 4.64(s, 2H), 4.85–5.2(m, 1H), 6.81(d, J=10Hz, 1H), 7.38(d, J=7Hz, 1H) |
| 25 | 1.24(d, J=6Hz, 3H), 1.45–1.75(m, 4H), 2.05–2.45(m, 5H), 2.28(s, 3H), 3.32(s, 3H), 3.35–3.5(m, 2H), 4.5–4.75(m, 2H), 4.67(s, 2H), 4.9–5.3(m, 1H), 6.84(d, J=10Hz, 1H), 7.44(d, J=7Hz, 1H) |
| 26 | 1.26(t, J=7Hz, 3H), 1.5–1.75(m, 4H), 2.1–2.4(m, 4H), 2.24(s, 3H), 3.74(s, 3H), 4.0(q, J=7Hz, 2H), 4.65(s, 2H), 6.85(d, J=10Hz, 1H), 7.27(d, J=7Hz, 1H) |
| 27 | 1.24(t, J=7Hz, 3H), 1.26(d, J=6Hz, 6H), 1.55–1.75(m, 4H), 2.1–2.4(m, 4H), 2.25(s, 3H), 3.94(q, J=7Hz, 2H), 4.65(s, 2H), 4.8–5.15(m, 1H), 6.84(d, J=10Hz, 1H), 7.34(d, J=7Hz, 1H) |
| 28 | 1.58(d, J=7Hz, 6H), 1.45–1.8(m, 4H), 2.2(s, 3H), 2.15–2.4(m, 4H), 3.72(s, 3H), 4.56(s, 2H), 4.6–5.0(m, 1H), 6.86(d, J=10Hz, 1H), 7.52(d, J=7Hz, 1H) |
| 29 | 1.25(d, J=7Hz, 3H), 1.49(d, J=7Hz, 6H), 1.45–1.75(m, 4H), 2.2(s, 3H), 2.1–2.5(m, 4H), 3.34(s, 3H), 3.36–3.48(m, 2H), 4.56(s, 2H), 4.6–5.15(m, 2H), 6.85(d, J=10Hz, 1H), 7.6(d, J=7Hz, 1H) |
| 30 | 1.5–1.7(m, 4H), 2.1–2.4(m, 4H), 2.25(s, 3H), 3.73(s, 3H), 4.05(m, 1H), 4.36(m, 2H), 4.68(s, 2H), 4.94(m, 1H), 6.85(d, J=10Hz, 1H), 7.33(d, J=7Hz, 1H) |
| 31 | 1.45–1.7(m, 4H), 2.1–2.4(m, 4H), 2.29(s, 3H), 3.36(s, 3H), 3.61(m, 2H), 4.08(m, 1H), 4.16–4.4(m, 4H), 4.68(s, 2H), 4.92(m, 1H), 6.85(d, J=10Hz, 1H), 7.39(d, J=7Hz, 1H) |
| 32 | 1.5–1.8(m, 4H), 2.15–2.45(m, 4H), 2.22(s, 3H), 3.32(s, 3H), 3.62(m, 2H), 3.74(s, 3H), 4.07(m, 2H), 4.67(s, 2H), 6.84(d, J=10Hz, 1H), 7.39(d, J=7HZ, 1H) |
| 33 | 1.45–1.75(m, 4H), 2.1–2.4(m, 4H), 2.27(s, 3H), 3.33(s, 3H), 3.38(s, 3H), 3.45–3.65(m, 4H), 3.9–4.1(m, 2H), 4.15–4.3(m, 2H), 4.68(s, 2H), 6.85(d, J=10Hz, 1H), 7.44(d, J=7Hz, 1H) |
| 34 | 1.45–1.8(m, 4H), 2.15–2.45(m, 4H), 2.22(s, 3H), 3.36(s, 3H), 3.6(m, 2H), 4.27(m, 2H), 4.4–4.6(m, 2H), 4.69(s, 2H), 5.0–5.3(m, 2H), 5.75–6.0(m, 1H), 6.85(d, J=10Hz, 1H), 7.26(d, J=7Hz, 1H) |
| 35 | 1.55(d, J=7Hz, 3H), 1.4–1.75(m, 4H), 2.18(s, 3H), 2.1–2.45(m, 5H), 3.37(s, 3H), 3.62(m, 2H), 4.32(m, 2H), 4.7(s, 2H), 4.9–5.2(m, 1H), 6.92(d, J=10Hz, 1H), 7.12(d, J=7Hz, 1H) |

A herbicide of the present invention containing N-acyl-N-phenyltetrahydrophthalamic acid derivatives [I] of the present invention as the effective component has a superior herbicidal activity against various weeds causing problems upon the submerged soil treatment in paddy fields, such as gramineous weeds such as noble (barnyardgrass, Echinochloa spp.), broad-leaved weeds such as azena (flase pimpernel, *Lindernia pyxidaria*), kikashigusa (toothcup, *Rotala indica*), mizohakobe (waterwort, *Elatine triandra*), cyperaceous weeds such as tamagayatsuri (small-flowered umbrellaplant, *Cyperus difformis*) and hotarui (bulrush, *Scirpus juncoides*), and weeds such as konagi (*Monochoria vaginalis*). Furthermore, the herbicide has a superior herbicidal activity against various weeds causing problems upon the foliage treatment and the soil treatment in uplands, such as broad-leaved weeds such as karashina (indian mustard, *Brassica juncea*), aobiyu (slender amaranth, *Amaranthus viridis*), hakobe (chickweed, *Stellaria media*), shiroza (common lambsquarters, *Chenopodium album*), onamomi (heartleaf cocklebur, *Xanthium strumarium*), maruba-asagao (tall morningglory, *Ipomoea purpurea*), yaemugura (catchweed bedstraw, *Galium aparine*), suberihiyu (common putslane, *Portulaca oleracea*), ichibi (velvetleaf, *Abutilon theophrasti*), amerika-tsunokusanemu (hemp sesbania, *Sesbania exaltata*), ebisugusa (sicklepod, *Cassia obtusifolia*), inuhouzuki (black nightshade, *Solanum nigrum*), spedwells, smart weeds, violets, tade (*Persicaria longiseta*) and its relatives, and sumire (*Viola mandshurica*) and its relatives, gramineous weeds such as inubie (barnyardgrass, *Echinochloa crus-galli*), enokorogusa (green foxtail, *Setaria viridis*), karasumugi (wild oat, *Avena fatua*), mehishiba (henry crabgrass, *Digitaria ciliaris*), seibanmorokoshi (johnsongrass, *Sorghum halepense*) and enbaku (oat, *Avena sativa*), cyperaceous weeds such as kogomegayatsuri (rice flatsedge, *Cyperus iria*) and hamasuge (nut grass, *Cyperus rotundus*), and commelinaceous weeds such as tsuyukusa (dayflower, *Commelina communis*). The herbicide of the present invention hardly injures major crops such as rice, wheat, corn and soybean.

Therefore, the herbicide of the present invention can be applied to upland, paddy field, orchard, pasture, turf, forest and non-crop land.

It is possible to process the herbicide of the present invention containing N-acyl-N-phenyltetrahydrophthalamic acid derivatives [I] as the effective component into an arbitrary form such as wettable powder, emulsion, granules, powder or flowable by using a pesticide adjuvant which is generally used in this field, such as an inactive solid carrier or liquid carrier and/or an emulsifying and dispersing agent and the like. As the inactive carriers, for example, talc, clay, bentonite, kaolin, diatomaceous earth, calcium carbonate, wood flour, starch, gum arabic, water, alcohol, kerosene, benzene, xylene, n-hexane, acetone,-dimethylformamide, glycol ether, N-methylpyrrolidone can be cited.

Besides, it is possible to adequately incorporate auxiliary agents for formulation, such as spreader, diluent, surfactant and solvent.

Upon using N-acyl-N-phenyltetrahydrophthalamic acid derivatives [I] of the present invention as a herbicide, a suitable application dosage is variable according to related factors such as manner of application, object of application, Lime of application and occurrence condition of weeds, but in general the application dosage, as expressed as the amount of the effective component, is preferably from 0.1 to 300 g, and particularly preferably from 1 to 300 g, per 10 ares.

Furthermore, to use the herbicide containing N-acyl-N-phenyltetrahydrophthalamic acid derivatives [I] of the present invention, it may be mixed with other herbicides, plant growth regulators, fungicides, insecticides, other pesticides, fertilizers and soil conditioners.

The following are Examples of herbicides according to the present invention, though compounds, carriers, adjuvants and the proportions of the ingredients are not limited to those in these examples. In these examples the amount of each component is indicated by parts by weight.

EXAMPLE 5 (Wettable Powder)

| | |
|---|---|
| Compound No. 5 | 10 parts |
| Sodium lignin sulfonate | 1.5 parts |
| Polyoxyethylene alkylaryl ether | 1.5 parts |
| Clay | 87 parts |

These materials were mixed together until a uniform mixture was obtained, and the mixture was pulverized to obtain a wettable powder.

EXAMPLE 6 (Granules)

| | |
|---|---|
| Compound No. 5 | 7 parts |
| Bentonite | 30 parts |
| Sodium alkylsulfonate | 2 parts |
| Clay | 61 parts |

These materials were mixed together and kneaded until a uniform mixture was obtained, and the mixture was granulated by an ordinary granulation method thereby to obtain granules.

EXAMPLE 7 (Emulsion)

| | |
|---|---|
| Compound No. 5 | 5 parts |
| N-methylpyrrolidone | 44 parts |
| Solpol 7065 | 43 parts |
| (product of Toho Kagaku Kogyo Co., Ltd.) | |
| Solpol 355 | 8 parts |
| (product of Toho Kagaku Kogyo Co., Ltd.) | |

These materials were mixed together until a uniform mixture was obtained, thereby to obtain an emulsion.

The following experiments are illustrative of the herbicidal effects of N-acyl-N-phenyltetrahydrophthalamic derivatives [I] of the present invention.

EXPERIMENT 1 (Flooded Soil Treatment)

Paddy soil (clay loam) was put into a pot so as to have a surface area of 1/15500 ares. Uniformly mixed seeds of several kinds of weeds, viz., nobie (barnyardgrass, Echinochloa spp.), broad-leaved weeds, hotarui (bulrush, *Scirpus juncoides*) and tamagayatsuri (small-flowered umbrella-plant, *Cyperus difformis*), were sown in the surface layer of the soil in each pot, and then paddy rice seedlings at the two- or three-leaved stage were transplanted into each pot to a depth of 2 cm, and water was fed into each pot so as to provide a 3 cm deep water layer on the soil surface. After 3 days, in other words at the initial stage of germination of nobie (barnyardgrass, Echinochloa spp.), a predetermined amount of a selected compound in the form of diluted aqueous solution was dropped into the water layer in each pot. After that, the pots were kept in a glass chamber to allow the paddy rice and the weeds to grow, and after the lapse of 4 weeks from the treatment with the selected compounds, the herbicidal effects and the degree of injury to the paddy rice were evaluated. The results are shown in Table 5. In the table, the herbicidal-effects and the degree of injury to the paddy rice are indicated by numerical values, which have the following meaning.

5: completely killed
4: seriously injured
3: considerably injured
2: somewhat injured
1: slightly injured
0: not injured (normally grown)

EXPERIMENT 2 (Foliage Treatment)

Upon seedling stage (two- or three-leaved stage) of rice, cockspur (*Panicum crus-galli*), garden radish, aobiyu (slender amaranth, *Amaranthus viridis*) and mehishiba (henry crabgrass, *Digitaria cliaris*) which were grown on a cultivated soil put in pots of 1/15500 ares, a selected compound in suspended wettable powder was sprayed to each plant. After that, the pots were kept in a glass chamber to allow each plant to grow, and after the lapse of 4 weeks from the treatment with the selected compounds the herbicidal effects were evaluated. The results are shown in Table 6. The evaluation of the herbicidal effects was similarly conducted as to that of Experiment 1.

EXPERIMENT 3 (Foliage Treatment)

Upon seedling stage (two- or three-leaved stage) of ichibi (velvetleaf, *Abutilon theophrasti*), onamomi (heartleaf cocklebur, *Xanthium strumarium*) (4L stage), noasagao (blue morningglory, *Ipomoea indica*) and ooinutade (pale smartweed, *Persicaria lapathifolia*) which were grown on a cultivated soil put in pots of 1/8850 ares, a selected compound in suspended wettable powder was sprayed to each plant. After that, the pots were kept in a glass chamber to allow each plant to grow, and after the lapse of 4 weeks from the treatment with the selected compounds the herbicidal effects were evaluated. The results are shown in Table 7. The evaluation of the herbicidal effects was similarly conducted as to that of Experiment 1.

TABLE 5

| Compound No. | Quantity of Compound g/10a | Injury of Paddy | Herbicidal Effect | | | |
|---|---|---|---|---|---|---|
| | | | nobie | broad-leaved weed | hotarui | tama-gaya-tsuri |
| 4 | 6.25 | 0.5 | 4.5 | 5 | 2 | 5 |
| | 3.13 | 0.5 | 4.5 | 4.5 | 1 | 3 |
| 5 | 6.25 | 1 | 5 | 5 | 4.5 | 5 |

TABLE 5-continued

| Compound No. | Quantity of Compound g/10a | Injury of Paddy | Herbicidal Effect | | | |
|---|---|---|---|---|---|---|
| | | | nobie | broad-leaved weed | hotarui | tama-gaya-tsuri |
| | 3.13 | 1 | 5 | 5 | 4.5 | 5 |
| 6 | 6.25 | 1 | 5 | 5 | 5 | 5 |
| | 3.13 | 0.5 | 5 | 5 | 4.5 | 5 |
| 7 | 6.25 | 2 | 5 | 5 | 4.5 | 5 |
| | 3.13 | 1 | 5 | 5 | 4 | 5 |
| 8 | 6.25 | 0.5 | 5 | 5 | 3 | 5 |
| | 3.13 | 0.5 | 5 | 4.5 | 2 | 5 |
| 9 | 6.25 | 3 | 5 | 5 | 4 | 5 |
| | 3.13 | 2 | 5 | 5 | 3 | 5 |
| 10 | 6.25 | 3 | 5 | 5 | 4 | 5 |
| | 3.13 | 1 | 5 | 5 | 3 | 5 |
| 11 | 6.25 | 2 | 5 | 5 | 4.5 | 5 |
| | 3.13 | 0.5 | 5 | 5 | 4 | 5 |
| 12 | 6.25 | 2 | 5 | 5 | 5 | 5 |
| | 3.13 | 2 | 5 | 5 | 5 | 5 |
| 13 | 6.25 | 4 | 5 | 5 | 5 | 5 |
| | 3.13 | 3 | 5 | 5 | 5 | 5 |
| 14 | 6.25 | 2 | 5 | 5 | 4.5 | 5 |
| | 3.13 | 1 | 5 | 5 | 4 | 5 |
| 21 | 6.25 | 2 | 5 | 5 | 4.5 | 5 |
| | 3.13 | 1 | 5 | 5 | 4.5 | 5 |
| 22 | 6.25 | 1 | 5 | 5 | 4 | 5 |
| | 3.13 | 1 | 5 | 5 | 3 | 5 |
| 23 | 6.25 | 3 | 5 | 5 | 4.5 | 5 |
| | 3.13 | 1 | 5 | 5 | 4 | 5 |
| 24 | 6.25 | 3 | 5 | 5 | 5 | 5 |
| | 3.13 | 1 | 5 | 5 | 4.5 | 5 |
| 25 | 6.25 | 1 | 4 | 5 | 4 | 5 |
| | 3.13 | 1 | 3 | 4.5 | 3 | 5 |
| 26 | 6.25 | 1 | 5 | 5 | 5 | 5 |
| | 3.13 | 1 | 5 | 5 | 4 | 5 |
| 27 | 6.25 | 4 | 5 | 5 | 5 | 5 |
| | 3.13 | 1 | 5 | 5 | 5 | 5 |
| 28 | 6.25 | 1 | 5 | 5 | 5 | 5 |
| | 3.13 | 0 | 4.5 | 5 | 4.5 | 5 |
| 29 | 6.25 | 2 | 5 | 5 | 4.5 | 5 |
| | 3.13 | 1 | 4 | 5 | 4.5 | 5 |
| 30 | 6.25 | 3 | 5 | 5 | 5 | 5 |
| | 3.13 | 1 | 5 | 5 | 4.5 | 5 |
| 31 | 6.25 | 2 | 5 | 5 | 4 | 5 |
| | 3.13 | 1 | 5 | 5 | 4 | 5 |
| 32 | 6.25 | 1 | 5 | 5 | 4.5 | 5 |
| | 3.13 | 1 | 5 | 5 | 4 | 5 |
| 33 | 6.25 | 1 | 5 | 5 | 4.5 | 5 |
| | 3.13 | 1 | 5 | 5 | 4.5 | 5 |
| 34 | 6.25 | 3 | 5 | 5 | 5 | 5 |
| | 3.13 | 1 | 5 | 5 | 4.5 | 5 |
| 35 | 6.25 | 1 | 4 | 5 | 4 | 5 |
| | 3.13 | 1 | 3 | 4.5 | 3 | 5 |

TABLE 6

| Compound No. | Quantity of Compound g/10a | rice | cockspur | garden radish | aobiyu | mehishiba |
|---|---|---|---|---|---|---|
| 4 | 80 | 1 | 0 | 5 | 5 | 1 |
| | 40 | 0.5 | 0 | 5 | 5 | 0 |
| 5 | 80 | 4 | 4.5 | 5 | 5 | 4.5 |
| | 40 | 4 | 4.5 | 5 | 5 | 4.5 |
| 6 | 80 | 3 | 2 | 5 | 5 | 5 |
| | 40 | 2 | 2 | 5 | 5 | 5 |
| 7 | 80 | 2 | 3 | 5 | 5 | 5 |
| | 40 | 1 | 3 | 5 | 5 | 5 |
| 8 | 80 | 1 | 1 | 1 | 5 | 3 |
| | 40 | 1 | 1 | 1 | 5 | 3 |
| 9 | 80 | 4.5 | 4.5 | 5 | 5 | 5 |
| | 40 | 4 | 2 | 5 | 5 | 5 |
| 10 | 80 | 2 | 3 | 5 | 5 | 3 |
| | 40 | 2 | 1 | 5 | 5 | 3 |
| 11 | 80 | 2 | 2 | 5 | 5 | 3 |
| | 40 | 2 | 2 | 5 | 5 | 3 |
| 12 | 80 | 2 | 2 | 5 | 5 | 3 |
| | 40 | 2 | 2 | 5 | 5 | 3 |
| 13 | 80 | 3 | 4.5 | 5 | 5 | 5 |
| | 40 | 3 | 3 | 5 | 5 | 5 |
| 14 | 80 | 2 | 2 | 5 | 5 | 2 |
| | 40 | 2 | 1 | 5 | 5 | 2 |
| 21 | 80 | 3 | 2 | 5 | 5 | 3 |
| | 40 | 2 | 1 | 5 | 5 | 1 |
| 22 | 80 | 1 | 2 | 2 | 5 | 3 |
| | 40 | 1 | 1 | 2 | 5 | 2 |
| 23 | 80 | 5 | 3 | 5 | 5 | 4 |
| | 40 | 4 | 1 | 5 | 5 | 2 |
| 24 | 80 | 4 | 5 | 5 | 5 | 5 |
| | 40 | 2 | 2 | 5 | 5 | 5 |
| 25 | 80 | 2 | 2 | 5 | 5 | 1 |
| | 40 | 1 | 1 | 5 | 5 | 1 |
| 26 | 80 | 3 | 3 | 5 | 5 | 3 |
| | 40 | 3 | 3 | 5 | 5 | 3 |
| 27 | 80 | 3 | 3 | 5 | 5 | 3 |
| | 40 | 2 | 2 | 5 | 5 | 2 |
| 28 | 80 | 3 | 4 | 5 | 5 | 4 |
| | 40 | 3 | 3 | 5 | 5 | 4 |
| 29 | 80 | 3 | 3 | 5 | 5 | 3 |
| | 40 | 3 | 2 | 5 | 4 | 2 |
| 30 | 80 | 3 | 3 | 4 | 5 | 4 |
| | 40 | 3 | 3 | 4 | 5 | 4 |
| 31 | 80 | 3 | 3 | 4 | 5 | 4 |
| | 40 | 3 | 3 | 4 | 5 | 4 |
| 32 | 80 | 3 | 3 | 5 | 5 | 4 |
| | 40 | 3 | 3 | 5 | 5 | 4 |
| 33 | 80 | 3 | 4 | 5 | 5 | 4 |
| | 40 | 3 | 3 | 5 | 5 | 4 |
| 34 | 80 | 3 | 4 | 5 | 5 | 4 |
| | 40 | 3 | 3 | 5 | 4 | 3 |
| 35 | 80 | 3 | 3 | 5 | 5 | 3 |
| | 40 | 2 | 2 | 4 | 4 | 3 |

TABLE 7

| Compound No. | Quantity of Compound g/10a | ichibi | onamomi | noasagao | ooinutade |
|---|---|---|---|---|---|
| 4 | 8 | 4 | 2 | 3 | 5 |
| | 4 | 3 | 1 | 3 | 5 |
| 5 | 8 | 5 | 5 | 5 | 5 |
| | 4 | 5 | 4 | 4.5 | 5 |
| 14 | 8 | 5 | 5 | 5 | 5 |
| | 4 | 5 | 5 | 4 | 5 |
| 21 | 8 | 5 | 5 | 4 | 5 |
| | 4 | 4.5 | 3 | 4 | 5 |
| 23 | 8 | 5 | 5 | 5 | 5 |
| | 4 | 5 | 5 | 5 | 5 |

INDUSTRIAL APPLICABILITY

N-acyl-N-phenyltetrahydrophthalamic acid derivatives of the present invention, which are novel compounds, exhibit excellent herbicidal activity, and are useful as a herbicide which can be widely applied to upland, paddy field, orchard, turf, forest, non-crop land, etc., and which is not harmful to crops.

We claim:

1. An N-acyl-N-phenyltetrahydrophthalamic acid derivative represented by the formula (I),

15

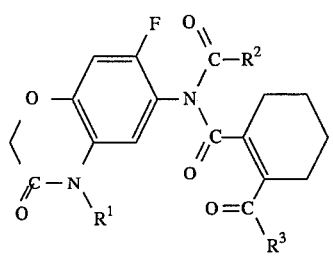 (I)

wherein R¹ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, R² represents a lower alkyl group or a halogenated lower alkyl group, and R³ represents a lower alkoxy group, a lower alkenyloxy group, a lower alkynyloxy group, a lower alkoxyalkoxy group, a benzyloxy group, a lower haloalkyloxy group or a lower alkoxycarbonylalkoxy group.

2. A method of producing an N-acyl-N-phenyltetrahydrophthalamic acid derivative which is represented by the formula (I), said method being characterized in that an imidoylchloride derivative represented by the general formula (II) is reacted with a carboxylic acid represented by the general formula (III) under the existence of a base,

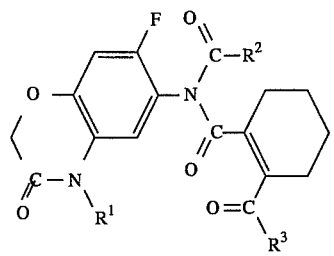 (I)

wherein R¹ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, R² represents a lower alkyl group or a halogenated lower alkyl group, and R³ represents a lower alkoxy group, a lower alkenyloxy group, a lower alkynyloxy group, a lower alkoxyalkoxy group, a benzyloxy group, a lower haloalkyloxy group or a lower alkoxycarbonylalkoxy group,

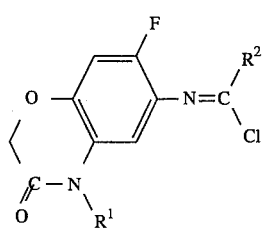 (II)

wherein R¹ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, and R² represents a lower alkyl group or a halogenated lower alkyl group,

16

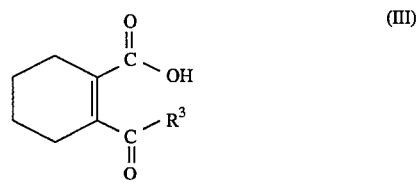 (III)

wherein R³ represents a lower alkoxy group, a lower alkenyloxy group, a lower alkynyloxy group, a lower alkoxyalkoxy group, a benzyloxy group, a lower haloalkyloxy group or a lower alkoxycarbonylalkoxy group.

3. A method of producing an N-acyl-N-phenyltetrahydrophthalamic acid derivative which is represented by the formula (I), said method being characterized in that an imidoylchloride derivative represented by the formula (II) is reacted with an alkali metal salt of a carboxylic acid represented by the formula (V),

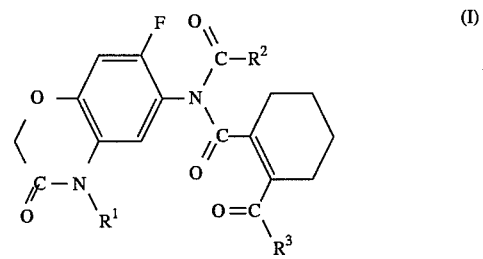 (I)

wherein R¹ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, R² represents a lower alkyl group or a halogenated lower alkyl group, and R³ represents a lower alkoxy group, a lower alkenyloxy group, a lower alkynyloxy group, a lower alkoxyalkoxy group, a benzyloxy group, a lower haloalkyloxy group or a lower alkoxycarbonylalkoxy group, (II)

wherein R¹ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, R² represents a lower alkyl group or a halogenated lower alkyl group, (V)

wherein R³ represents a lower alkoxy group, a lower alkenyloxy group, a lower alkynyloxy group, a lower alkoxyalkoxy group, a benzyloxy group, a lower haloalkyloxy group or a lower alkoxycarbonylalkoxy group, and M represents an alkali metal.

4. An imidoylchloride derivative represented by the formula (II),

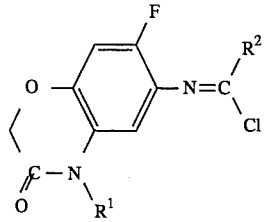

(II)

wherein $R^1$ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group and $R^2$ represents a lower alkyl group or a halogenated lower alkyl group.

5. A method of producing an imidoylchloride derivative represented by the formula (II), said method being characterized in that an anilide derivative represented by the formula (IV) is reacted under the existence of a dehydrochlorinating agent,

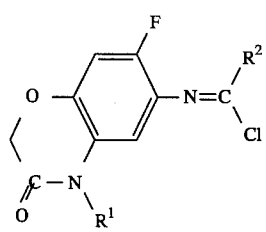

(II)

wherein $R^1$ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group and $R^2$ represents a lower alkyl group or a halogenated lower alkyl group,

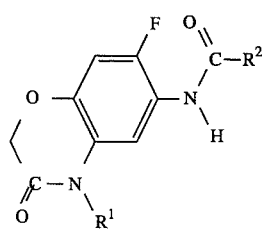

(IV)

wherein $R^1$ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, and $R^2$ represents a lower alkyl group or a halogenated lower alkyl group.

6. A method of producing an imidoylchloride derivative according to claim 4, said method being characterized in that said dehydrochlorinating agent is phosphorus pentachloride, phosphorus trichloride-chlorine, thionyl chloride, arylsulfonyl chloride, phosgene, triphenylphosphine-carbon tetrachloride or polymer-carried triphenylphosphine-carbon tetrachloride.

7. A herbicidal composition comprising, as an effective component, an N-acyl-N-phenyltetrahydrophthalamic acid derivative which is represented by the formula (I) and an inactive carrier diluent,

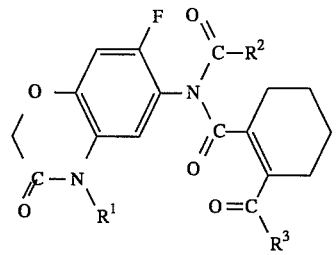

(I)

wherein $R^1$ represents an alkyl group, an alkenyl group, an alkynyl group, an alkoxyalkyl group, a haloalkyl group, a haloalkenyl group, a haloalkynyl group or a cyanoalkyl group, each said alkyl, alkenyl or alkynyl group being a $C_1$–$C_4$ group, $R^2$ represents a lower alkyl group or a halogenated lower alkyl group, and $R^3$ represents a lower alkoxy group, a lower alkenyloxy group, a lower alkynyloxy group, a lower alkoxyalkoxy group, a benzyloxy group, a lower haloalkyloxy group or a lower alkoxycarbonylalkoxy group.

8. A herbicidal composition according to claim 7, which is in the form of a wettable powder comprising an inactive carrier.

9. A herbicidal composition according to claim 7, which is in the form of granules comprising an inactive carrier.

10. A herbicidal composition according to claim 7, which is in the form of an emulsion comprising an inactive carrier.

11. A herbicidal composition according to claim 7, wherein said N-acyl-N-phenyltetrahydrophthalamic acid derivative is N-(2-chloroacetyl)-N-(7-fluoro-4-cyanomethyl-2H-1,4-benzoxazine-3(4H)-one-6-yl)-3,4,5,6-tetrahydrophthalamic acid methyl ester.

12. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3(4H)-one-6-yl)-3,4,5,6-tetrahydrophthalamic acid methyl ester.

13. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3 (4H)-one-6-yl)-3,4,5,6-tetrahydrophthalamic acid propargyl ester.

14. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3(4H)-one-6-yl)-3,4,5,6-tetrahydrophthalamic acid-n-butyl ester.

15. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3(4H)-one-6-yl)-3,4,5,6-tetrahydrophthalamic acid benzyl ester.

16. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3(4H)-one-6-yl)-3,4,5,6-tetrahydrophthalamic acid ethyl ester.

17. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3 (4H)-one-6-yl)-3,4,5,6-tetrahydrophthalamic acid ethoxycarbonylmethyl ester.

18. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3 (4H)-one-6-yl)-3,4,5,6-tetrahydrophthalamic acid allyl ester.

19. A herbicidal composition according to claim 7, wherein said N-acyl-N-phenyltetrahydrophthalamic acid derivative is N-(2-chloroacetyl)-N-(7-fluoro-4-propargyl-2H-1,4-benzoxazine-3(4H)-one-6-yl)-3,4,5,6-tetrahydrophthalamic acid-2-methoxyethyl ester.

20. A herbicidal composition according to claim 7, wherein said N-acyl-N-phenyltetrahydrophthalamic acid derivative is N-(2chloroacetyl)-N-(7-fluoro-4-propargyl-2H-1,4-benzoxazine-3 (4H)-one-6-yl)-3,4,5,6-tetrahydrophthalamic acid isopropyl ester.

21. A herbicidal composition according to claim 7, wherein said N-acyl-N-phenyltetrahydrophthalamic acid derivative is N-acetyl-N-(7-fluoro-4-propargyl-2H-l,4-benzoxazine-3 (4H)-one-6-yl)-3,4,5,6-tetrahydrophthalamic acid methyl ester.

22. A herbicidal composition according to claim 7, wherein said N-acyl-N-phenyltetrahydrophthalamic acid derivative is N-acetyl-N-(7-fluoro-4-propargyl-2H-1,4-benzoxazine-3 (4H)-one-6-yl)-3,4,5,6-tetrahydrophthalamic acid-n-butyl ester.

23. A herbicidal composition according to claim 7, wherein said N-acyl-N-phenyltetrahydrophthalamic acid derivative is N-acetyl-N-(7-fluoro-4-propargyl-2H-1,4-benzoxazine-3 (4H)-one-6-yl)-3,4,5,6-tetrahydrophthalamic acid benzyl ester.

24. A herbicidal composition according to claim 7, wherein said N-acyl-N-phenyltetrahydrophthalamic acid derivative is N-acetyl-N-(7-fluoro-4-propargyl-2H-1,4-benzoxazine-3 (4H)-one-6-yl)-3,4,5,6-tetrahydrophthalamic acid-2-methoxyethyl ester.

25. A herbicidal composition according to claim 7, wherein said N-acyl-N-phenyltetrahydrophthalamic acid derivative is N-acetyl-N-(7-fluoro-4-propargyl-2H-1,4-benzoxazine-3 (4H)-one-6-yl)-3,4,5,6-tetrahydrophthalamic acid isopropyl ester.

26. A herbicidal composition according to claim 7, wherein said N-acyl-N-phenyltetrahydrophthalamic acid derivative is N-acetyl-N-(7-fluoro-4-propargyl-2H-1,4-benzoxazine-3 (4H)-one-6-yl)-3,4,5,6-tetrahydrophthalamic acid-1-methyl-2methoxyethyl ester.

27. A herbicidal composition according to claim 7, wherein said N-acyl-N-phenyltetrahydrophthalamic acid derivative is N-acetyl-N-(7-fluoro-4-ethyl-2H-1,4-benzoxazine-3(4H)-one-6-yl)-3,4,5,6-tetrahydrophthalamic acid methyl ester.

28. A herbicidal composition according to claim 7, wherein said N-acyl-N-phenyltetrahydrophthalamic acid derivative is N-acetyl-N-(7-fluoro-4-ethyl-2H-1,4-benzoxazine-3(4H)-one-6-yl)-3,4,5,6-tetrahydrophthalamic acid isopropyl ester.

29. A herbicidal composition according to claim 7, wherein said N-acyl-N-phenyltetrahydrophthalamic acid derivative is N-acetyl-N-(7-fluoro-4-isopropyl-2H-1,4-benzoxazine-3 (4H)-one-6-yl)-3,4,5,6-tetrahydrophthalamic acid methyl ester.

30. A herbicidal composition according to claim 7, wherein said N-acyl-N-phenyltetrahydrophthalamic acid derivative is N-acetyl-N-(7-fluoro-4-isopropyl-2H-1,4-benzoxazine-3(4H)-one-6 -yl)-3,4,5,6-tetrahydrophthalamic acid-1-methyl-2methoxyethyl ester.

31. A-herbicidal composition according to claim 7, wherein said N-acyl-N-phenyltetrahydrophthalamic acid derivative is N-acetyl-N-[7-fluoro-4-(2-fluoroethyl)-2H-1,4-benzoxazine-3 (4H)-one-6-yl)-3,4,5,6-tetrahydrophthalamic acid methyl ester.

32. A herbicidal composition according to claim 7, wherein said N-acyl-N-phenyltetrahydrophthalamic acid derivative is N-acetyl-N-[7-fluoro-4-(2-fluoroethyl)-2H-1,4-benzoxazine-3 (4H)-one-e-yl)-3,4,5,6-tetrahydrophthalamic acid-2methoxyethyl ester.

33. A herbicidal composition according to claim 7, wherein said N-acyl-N-phenyltetrahydrophthalamic acid derivative is N-acetyl-N-[7-fluoro-4-(2-methoxyethyl)-2H-1,4-benzoxazine-3 (4H)-one-6-yl)-3,4,5,6-tetrahydrophthalamic acid methyl ester.

34. A herbicidal composition according to claim 7, wherein said N-acyl-N-phenyltetrahydrophthalamic acid derivative is N-acetyl-N-[7-fluoro-4-(2-methoxyethyl)-2H-1,4-benzoxazine-3 (4H)-one-6-yl)-3,4,5,6-tetrahydrophthalamic acid-2methoxyethyl ester.

35. A herbicidal composition according to claim 7, wherein said N-acyl-N-phenyltetrahydrophthalamic acid derivative is N-acetyl-N-(7-fluoro-4-allyl-2H-1,4-benzoxazine-3(4H)-one-6-yl)-3,4,5,6-tetrahydrophthalamic acid-2-methoxyethyl ester.

36. A herbicidal composition according to claim 7, wherein said N-acyl-N-phenyltetrahydrophthalamic acid derivative is N-acetyl-N-[7-fluoro-4-(1-methylpropargyl)-2H-1,4 -benzoxazine-3(4H)-one-6-yl)-3,4,5,6-tetrahydrophthalamic acid-2-methoxyethyl ester.

\* \* \* \* \*